United States Patent
Guerout et al.

(10) Patent No.: US 8,857,246 B2
(45) Date of Patent: Oct. 14, 2014

(54) PORTABLE POLYMER TESTER

(75) Inventors: Fabrice Guerout, Deep River (CA); Ladjl Cisse, Deep River (CA); Richard Boor, Deep River (CA)

(73) Assignee: Atomic Energy of Canada Limited, Mississauga, Ontario (CA)

( * ) Notice: Subject to any disclaimer, the term of this patent is extended or adjusted under 35 U.S.C. 154(b) by 631 days.

(21) Appl. No.: 13/129,196

(22) PCT Filed: Nov. 16, 2009

(86) PCT No.: PCT/CA2009/001654
§ 371 (c)(1),
(2), (4) Date: Dec. 21, 2011

(87) PCT Pub. No.: WO2010/054486
PCT Pub. Date: May 20, 2010

(65) Prior Publication Data
US 2012/0085155 A1    Apr. 12, 2012

Related U.S. Application Data

(60) Provisional application No. 61/114,889, filed on Nov. 14, 2008.

(51) Int. Cl.
*G01N 3/42*    (2006.01)
*G01N 33/44*   (2006.01)
*G01N 3/40*    (2006.01)

(52) U.S. Cl.
CPC .............. *G01N 3/405* (2013.01); *G01N 33/445* (2013.01); *G01N 2203/0286* (2013.01); *G01N 3/42* (2013.01); *G01N 2203/0222* (2013.01)
USPC ........................................................... 73/82

(58) Field of Classification Search
USPC ...................................................... 73/81, 82
See application file for complete search history.

(56) References Cited

U.S. PATENT DOCUMENTS 2,372,662 A    4/1945  Dewey
3,102,417 A    9/1963  Chambers
(Continued)

FOREIGN PATENT DOCUMENTS

EP    1 178 299    2/2002
JP    62-132146    6/1987
(Continued)

OTHER PUBLICATIONS

Bertrand et al. (1995) "Non Destructive Control Applied on Power Station Cables: Assessment of the Residual Mechanical Properties of Cables," http://www.see.asso.fr/jicable/TOUT_JICABLE_FIRST_PAGE/1995/115-B10-1_page1.pdf.

(Continued)

*Primary Examiner* — Hezron E Williams
*Assistant Examiner* — David Z Huang
(74) *Attorney, Agent, or Firm* — Lathrop & Gage LLP

(57) ABSTRACT

The present invention provides a polymer indentation method and tester that includes measuring the time taken by a polymeric material to recover a set portion of an initial deformation and use this duration as a material degradation indicator. The recovery time was found to be more sensitive to cable degradation than the specific compressive stiffness (or indenter modulus) measured during the indentation phase, and this high sensitivity was achieved for both thermally aged and irradiated polymer samples.

22 Claims, 18 Drawing Sheets

(56) References Cited

U.S. PATENT DOCUMENTS

| | | | |
|---|---|---|---|
| 3,658,425 | A | 4/1972 | Bird et al. |
| 3,956,925 | A | 5/1976 | Smith |
| 4,848,141 | A | 7/1989 | Oliver et al. |
| 5,067,346 | A | 11/1991 | Field |
| 5,357,786 | A | 10/1994 | Lung et al. |
| 6,247,356 | B1 | 6/2001 | Merck, Jr. et al. |
| 6,332,364 | B1 | 12/2001 | Buschmann et al. |
| 6,513,369 | B1 | 2/2003 | Chew |
| 6,668,662 | B2 | 12/2003 | Isogai et al. |
| 6,755,075 | B2 | 6/2004 | Nagashima et al. |
| 6,945,097 | B2 | 9/2005 | Jardret et al. |
| 2003/0009300 | A1* | 1/2003 | Giurgiutiu ............ 702/35 |
| 2004/0011119 | A1 | 1/2004 | Jardret et al. |
| 2007/0193346 | A1* | 8/2007 | Bonin ............ 73/81 |
| 2007/0278866 | A1* | 12/2007 | Ida et al. ............ 310/12 |
| 2008/0028840 | A1* | 2/2008 | Smith et al. ............ 73/81 |

FOREIGN PATENT DOCUMENTS

| | | |
|---|---|---|
| JP | 2-38947 | 3/1990 |
| JP | 2001-221730 | 8/2001 |
| JP | 2002-357520 | 12/2002 |
| JP | 2003-185547 | 7/2003 |
| JP | 2004-500543 | 1/2004 |
| JP | 2004-228265 | 8/2004 |
| JP | 2005-024384 | 1/2005 |
| JP | 2005-522690 | 7/2005 |
| JP | 2005-249590 | 9/2005 |
| JP | 2007-139522 | 6/2007 |
| WO | WO 00/17621 | 3/2000 |
| WO | WO 03/087778 | 10/2003 |

OTHER PUBLICATIONS

Bouaita et al. (Sep. 2006) "Dynamic Nanoindentation of Some Polyolefins," *Poly. Eng. Sci.* 46(9):1160-1172.

Denny (Oct. 2004) "Material Testing Research and Indenter Equipment Modifications for Determining Aging of Wires (Cables) in Aircraft," US Department of Transportation, Federal Aviation Administration, Office of Aviation Research, Report # DOT/FAA/AR-04/17.

Gazdinski et al., Sandia National Laboratories / U.S. Department of Energy (Sep. 1996) "Aging Management Guidelines for Commercial Nuclear Power Plants—Electrical Cable and Terminations," SAND96-0344.

International Search Report and Preliminary Report on Patentability, Corresponding to International Application No. PCT/CA2009/001654, Mailed Mar. 3, 2010.

International Atomic Energy Agency (Dec. 2000) "Assessment and Management of Ageing of Major Nuclear Power Plant Components Important to Safety: In-Containment Instrumentation and Control Cables," col. 1, IAEA-TECDOC-1188.

Kim, J.S. (Aug. 2005) "Evaluation of Cable Aging Degradation Based on Plant Operating Condition," *J. Nuc. Sci. Technol.* 42(8):745-753.

Kim et al. (Oct. 2004) "Evaluation of Nuclear Plant Aging Through Condition Monitoring," *J. Korean Nuc. Soc.* 36(5):475-484.

Nuclear Energy Agency, Committee on the Safety if Nuclear Installations (2004) "Research Efforts Related to Wire Systems Aging in NEA Member Countries," Report NEA/CSNI/R (2004)12, Aug. 11.

Toman et al., Electric Power Research Institute (Jan. 1996) "Evaluation of Cable Polymer Aging Through Indenter Testing of In-Plant and Laboratory Aged Specimens," EPRI TR-104075.

Notification of Reasons for Refusal dispatched Jul. 23, 2013, from the Japanese Patent Office for Japanese Patent Application No. 2011-535846.

\* cited by examiner

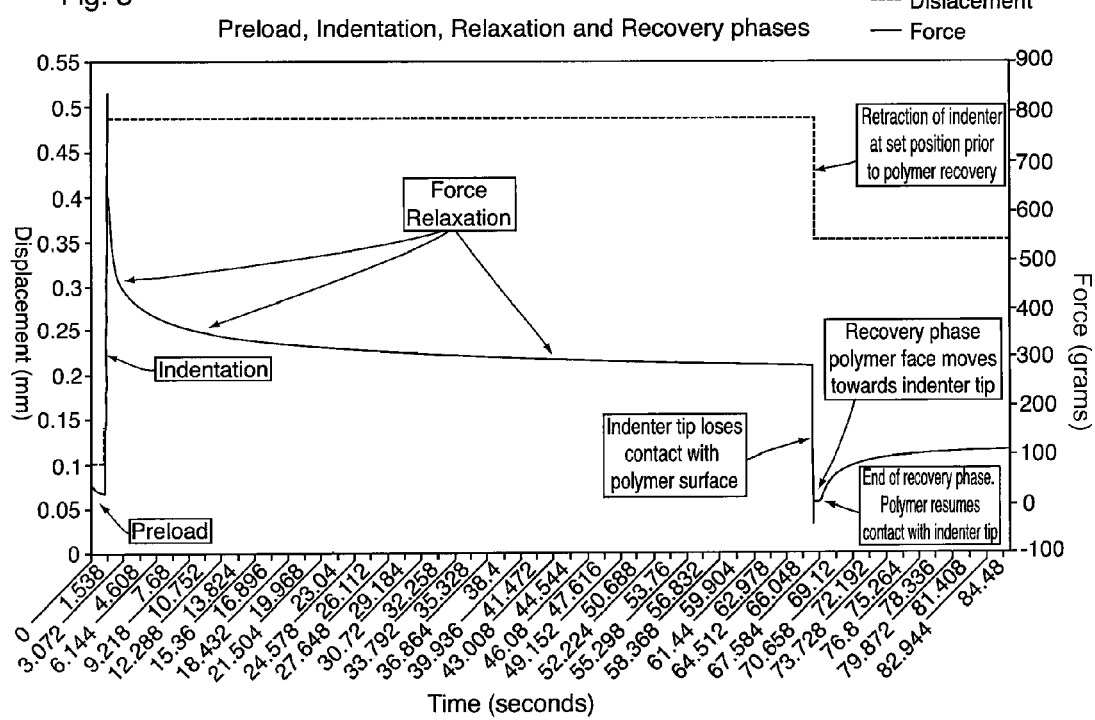

Fig. 4C
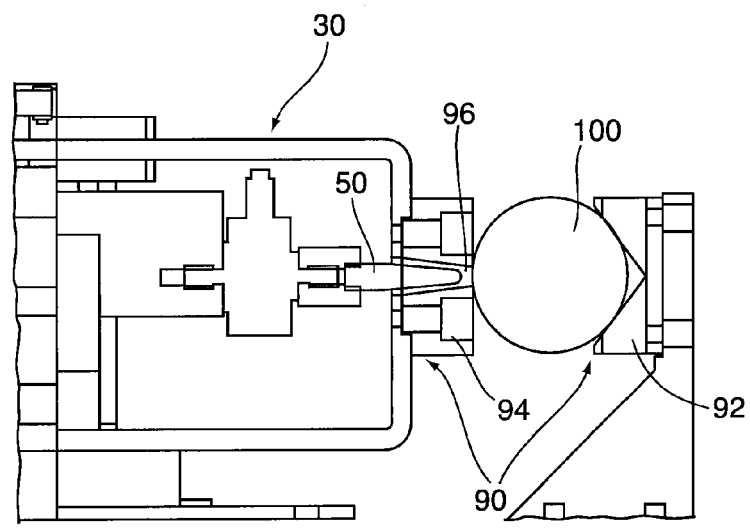
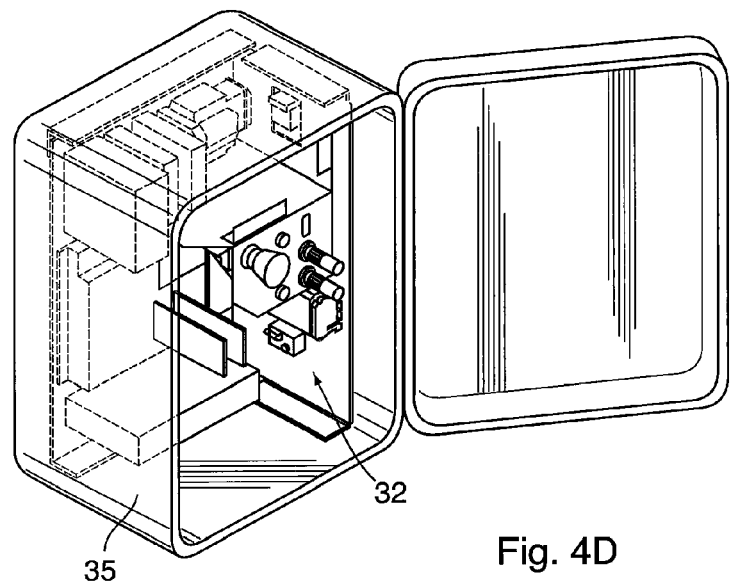
Fig. 4D

Fig. 16A
Fig. 16B
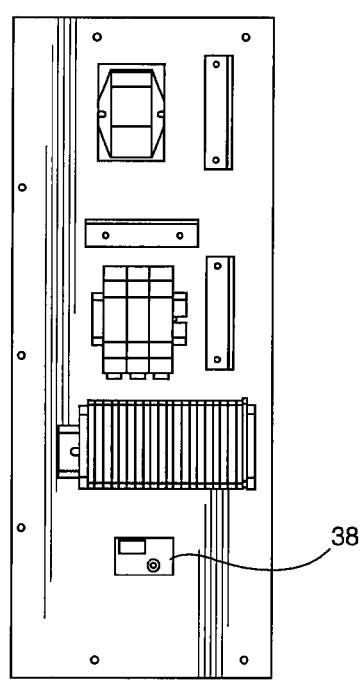
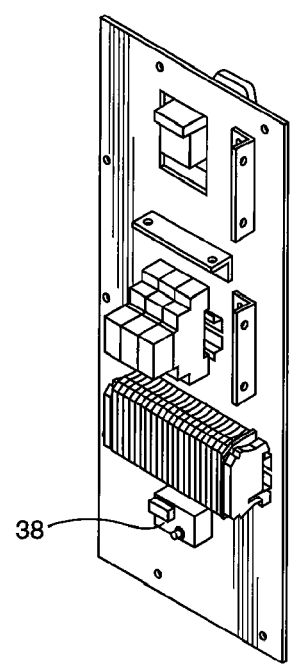

PORTABLE POLYMER TESTER

CROSS-REFERENCE TO RELATED APPLICATION

This application claims the benefit and priority to U.S. provisional patent application No. 61/114,889, filed Nov. 14, 2008, which is incorporated herein in its entirety as though set forth explicitly herein.

FIELD OF THE INVENTION

The present invention pertains to the field of polymer material testing and, more particularly to the field of portable polymer testers for in-situ monitoring of polymer-based components.

BACKGROUND

The aging of polymers is of considerable importance to, among others, industrial and electrical power plant operators in that the unanticipated failure of such polymers may have significant adverse effects on human safety, plant operation and maintenance costs and downtime. Polymers are used in key components related to the safe and reliable operation of industrial and power plants. Specifically, polymers are found in, but not limited to; cables, pumps, valves and seals.

Electrical and optical cables, such as power, control, instrumentation and data transmission have traditionally been considered long-lived components which merit little in the way of preventive maintenance or condition monitoring due to their generally high level of reliability and simplicity of construction. Like all other components, however, such cables age as a result of operational and environmental stressors. The typical modes of degradation due to cable aging are embrittlement leading to cracks, loss of dielectric strength, and increased leakage current. The main stressors causing age-related degradation are thermal aging resulting from elevated temperatures and ionising radiation. Other degradation stressors of cables include mechanical stresses, humidity, hydrocarbon fluids, and ozone.

Aging effects may be spatially generalized (i.e., affecting most or all portions of a given cable equally, such as for a cable located completely within a single room of uniform temperature), or localized (i.e., affecting only very limited portions of a cable, such as in the case of a cable routed near a highly localized heat source). The severity of these aging effects depends on several factors including the severity of the stressor, the materials of construction and design of the cable, and the ambient environment surrounding the cable. Detailed discussions of electrical cable aging may be found in a number of publications including Kim, J-S., "Evaluation of Cable Aging in Degradation Based Plant Operating Condition" (2005) *J. Nucl. Sci. Technol.* 42(8) 745-753 and SAND96-0344 "Aging Management Guideline for Commercial Nuclear Power Plants—Electrical Cable and Terminations" prepared by Sandia National Laboratories/U.S. Department of Energy, September 1996. Discussions regarding optical cable aging may be found, inter alia, in Electric Power Research Institute (EPRI) publications and telecommunications industry literature. The following description will be limited to electrical cable, although it can be appreciated that the principles of aging and analysis described herein may also be largely applicable to optical cabling.

A typical instrumentation and control (I&C) cable consists of multi-conductor assemblies insulated with fire-retardant material with an overall shield and an outer jacket. In addition, the cables used in plants such as nuclear reactor stations may contain tape wraps that enhance electrical, mechanical, or fire protection properties.

Insulation and jacket materials used for I&C cables are polymers that contain additives and fillers to improve aging resistance, electrical, mechanical and fire retardant properties. The most widely used jacket and insulation materials in older CANDU® plants are polyvinyl chloride (PVC). In newer plants the materials are chlorosulphonated polyethylene (CSPE), also know as Hypalon™ for the jackets and cross-linked polyethylene/polyolefin (XLPE/XLPO), and ethylene-propylene based elastomers (EPR, EPDM) for the insulation.

The level of degradation of the insulation and jacket materials attributed to aging depends upon the polymer compound used (presence of adequate additives, etc.), the pre-service (storage) and service environmental conditions (temperature, radiation, mechanical stress, humidity), and the elapsed service life (time factor). The main chemical aging mechanisms of polymers result from scission, cross-linking, and oxidation reactions at the molecular level. The scission of alkoxyl or peroxide radicals usually leads to the scission of one macromolecular chain into two new chains. Cross-linking refers to the formation of covalent links between adjacent macromolecules and the formation of a dense network of chains. Oxidation reactions, which start from the formation of free radicals (because of the initial break of a covalent link under the effect of temperature and/or radiation), can lead either to chain scission or cross-linking. The organic materials usually undergo physical changes such as hardening and loss of flexibility as a result of exposure to heat and radiation. Another type of physical aging mechanism due to thermal aging is the evaporation and possible migration of plasticizers in PVC materials.

The level of degradation of a material can be assessed by tracking the changes of material properties. Some standard techniques used include: visual and tactile inspections, tensile tests, indentation tests, differential scanning calorimetry, Fourier Transform Infrared Reflectance (FTIR) Spectroscopy, measurement of swelling ratio, mass loss, plasticizer content, dielectric measurements or change in density.

One of the most commonly used laboratory techniques to assess degradation is tensile testing, which consists of comparing the percentages of elongation at break (EAB) or the tensile strength for unaged and aged samples. EAB is a proven degradation indicator and an accepted parameter for the estimation of the residual lifetime of a cable. End-of-life criteria based on this parameter are well established. An ultimate EAB of 50% is usually used as an end point criterion [International Atomic Energy Agency, 2000, "Assessment and Management of Ageing of Major Nuclear Power Plant Components Important to Safety: In-Containment Instrumentation and Control Cables", Volume 1, IAEA-TECDOC-1188, December]. The main disadvantage is the large sample size required and the destructive aspect of the technique.

The number of techniques available for on-site monitoring is limited because of the strong requirement from station personnel to use non-destructive and non-intrusive techniques. Another difficulty is that some of the instruments typically used in the laboratory environment are not easily portable to site.

Over the past few years, various panels of international experts were formed to review existing data and the state of advancement of current condition monitoring techniques [IAEA-TECDOC-1188, 2000 (above) and Nuclear Energy Agency, Committee on the Safety of Nuclear Installations, 2004, "Research Efforts Related to Wire Systems Aging in NEA Member Countries", Report NEA/CSNI/R, (2004)12, August 11]. These panels provided guidelines and recommendations with respect to the orientation of Research and Development (R&D) programs to address cable aging issues. The recommendations for future research and development efforts to address this issue were as follows [Report NEA/CSNI/R, 2004 (above)]:

Continue the development of new, effective, in-situ condition monitoring techniques for installed wire systems that can be used to determine the current condition of a wire system and predict its useful life. In this regard, advanced electrical, optical, ultrasonic and aerospace technologies should be evaluated and developed for nuclear plant applications; and Correlate mechanical wire system properties to electrical properties to better understand the significance of reaching the limits of mechanical properties for aged insulating materials.

Some of the physical techniques used to analyse cable polymer aging, such as the measurement of the tensile strength or elongation-at-break of the insulation material are inherently destructive and require a specimen of the aged cable for testing. However, there are some non-destructive physical techniques, including the measurement of compressive modulus, torsional modulus, or rigidity under bending, that do demonstrate a correlation between the aging of the cable and the measured parameter (especially for low-voltage cable), and can be practical to apply during operational conditions. For example, the measurement of compressive modulus by way of instruments such as the Indenter Polymer Aging Monitor can be useful for measurement of cable polymer aging. See, for example, EPRI TR-104075, "Evaluation of Cable Polymer Aging Through Indenter Testing of In-Plant and Laboratory Aged Specimens," prepared by the Electric Power Research Institute, January, 1996 for a discussion of the correlation between outer jacket and conductor physical measurements.

The portable indenters currently used are generally limited to the sole measurement of material stiffness or hardness. However, for some polymer-based materials, the stiffness/hardness remains unchanged with increasing irradiation level, even though basic material properties such as the elongation at break clearly indicate a continuous degradation resulting from this stressor. Likewise, when polymeric components are subjected to thermal aging, the stiffness sometimes increases initially but quickly reaches a saturation value, even though it is known that further degradation continues to occur. Therefore, the indenters currently available are not ideally suited for the monitoring of cable aging.

In an indenter made by Electric Power Research Institute (EPRI) the limit of indentation depth is controlled based on the value of the force measured. Therefore the indentation depth varies between an unaged and an aged elastomer. This prevents the study of recovery of the elastomer for a fixed reference indentation depth. The EPRI indenter can be used to monitor a portion of the force signal after the maximum force is reached and the force starts to relax and decay. The probe can be held in position during the relatively short relaxation period that is being analysed. However, the force relaxation features do not change significantly with increased aging of the material.

With the EPRI indenter, once the relaxation information is acquired, the probe is slowly driven back to original position and no further investigation takes place. Because of the nature of the drive system, the probe cannot be retracted instantly or quickly from a given reference position. Therefore it is not possible to create conditions that permit assessment of recovery of deformation following the force relaxation phase when using the EPRI indenter.

In addition, current portable indenters do not offer the flexibility of changing the type of excitation signals, nor programming a variety of sequences of events for the indenter probe. This is detrimental to the systematic identification of optimal input parameters, set-ups, and output parameters in terms of their sensitivity to polymer degradation.

Based on the foregoing, there remains a need for a method and device for monitoring and estimating the aging of polymer cable, which method and device is portable, non-destructive and permits optimization and measurement of characteristics other than merely polymer stiffness.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a portable polymer tester. In accordance with one aspect of the invention, there is provided a method and device for indenting polymer material, such as cable insulation or cable jacket material, to generate indentation and post-indentation parameters that characterize the visco-elastic properties of the polymer material tested. The visco-elastic properties are used as an indicator of polymer age and degradation. The method and device of the present invention measures stiffness (measurement of force and displacement) of polymeric material, as well as the time taken by the polymeric material to recover a set portion of the initial deformation. This duration can be used as an indicator of polymer material degradation.

In accordance with an aspect of the present invention, there is provided a polymer tester for measuring physical characteristics of a polymer material, such as a polymer jacket of a cable, said polymer tester comprising: jaw assemblies for retaining a sample, such as a cable or a flat elastomeric sample, during testing; an interchangeable and moveable probe; a drive system for advancing the probe to contact and deform the polymer jacket of the cable, said drive system comprising a motor and a linear slide and stage (for example, a ceramic servo motor and a nanostage); and a force/displacement measurement system including means for measuring force at the tip of said probe during contact with said polymer jacket and means for measuring displacement of the probe.

In accordance with another aspect of the invention, there is provided a method for testing polymer aging, such as cable polymer aging, comprising the steps of: immobilizing a polymer material (such as a polymer jacket in the case of testing cable aging); deforming a region of the polymer using a probe; calculating stiffness of the polymer from measured displacement of the probe and force at the tip of said probe during deformation; retracting said probe to a predetermined position and measuring time of recovery of deformation; wherein the stiffness and the time of recovery of deformation are indicators of degree of polymer aging.

BRIEF DESCRIPTION OF THE FIGURES

FIG. 3 graphically depicts an indenter test cycle according to one embodiment of the present invention.

FIG. 16 shows drawings of the side panel of a control chassis showing the mounting and wiring (16A is a face view and 16B is a perspective view).

DETAILED DESCRIPTION OF THE INVENTION

Unless defined otherwise, all technical and scientific terms used herein have the same meaning as commonly understood by one of ordinary skill in the art to which this invention belongs.

Unless the context clearly indicates otherwise, as used herein plural forms of the terms herein are to be construed as including the singular form and vice versa.

The term "comprising" as used herein will be understood to mean that the list following is non-exhaustive and may or may not include any other additional suitable items, for example one or more further feature(s), component(s) and/or part(s) as appropriate.

The portable polymer tester ("PPT") of the present invention was developed to take advantage of an indentation technique that includes the option of programming and controlling a variety of input parameters, a variety of sequence of events for the probe displacement and the access to a variety of output parameters. The PPT of the present invention is a controllable tool (in comparison to tools currently in use) that can be configured to measure parameters most prone to tracing the degradation of polymer-based components and is fully portable to allow for the measurement of these parameters on site.

The PPT of the present invention incorporates means for classical measurement of material stiffness (or modulus) via linear drive of an indenter probe into the material (once the probe has been slightly preloaded onto the sample surface). The stiffness parameter is derived from simultaneous acquisition of the probe reaction force and probe displacement during the indentation phase. The PPT also incorporates means for measurement of post-indentation parameters such as force relaxation and recovery of deformation.

The indentation technique for monitoring polymer or elastomer material degradation, is a quantitative non-destructive monitoring technique that basically comprises driving a probe tip onto the surface of the polymer or elastomer material, for example a cable jacket or cable insulation material [IAEA-TECDOC-1188, 2000 (above)]. The technique provides one or more of the following advantages:

portable instruments can be developed,
the measurement is quick, and
data are easy to analyse.

During the indentation phase, the force and the probe displacement are measured to derive a specific compressive stiffness parameter, also called the "indenter modulus". This parameter shows some correlation with polymer or elastomer degradation for most cable materials used in, for example, nuclear power plants, but the sensitivity of the technique can be limited. Two notable exceptions are materials for which the indenter modulus values tend to stay constant (e.g., irradiated PVC) or only change for a severely degraded material (e.g., thermally aged XLPE).

Figure 1:
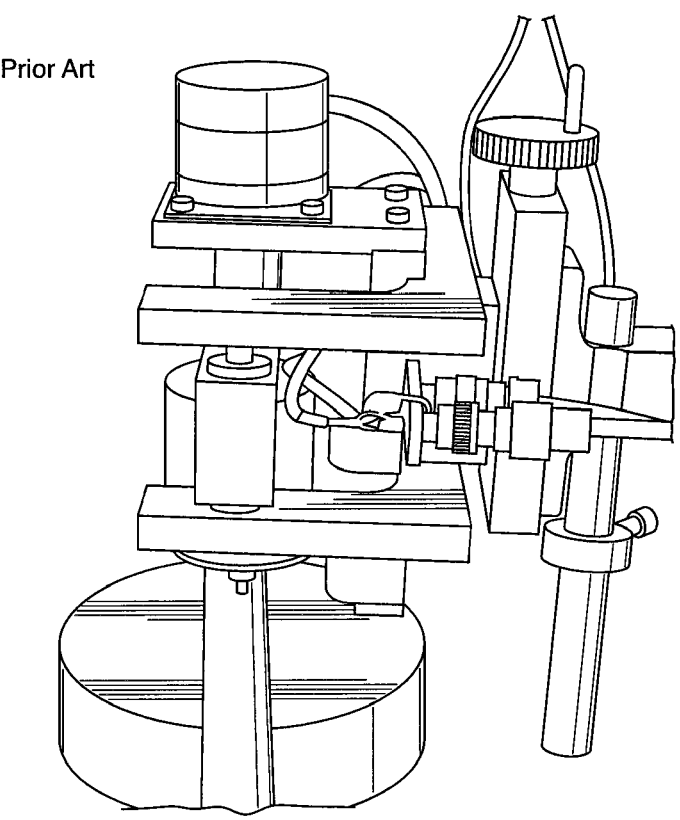
FIG. 1 is a photograph of the Elasto-Dynamic Spot Tester, a precursor tool to the device of the present invention.

An on-site laboratory indenter, referred to as the Elasto-Dynamic Spot Tester (EDST), has been previously developed. Initially, the EDST was used to derive the elastomer spot stiffness during indentation and also to study various post-indentation visco-elastic properties, such as the percentage of force relaxed after a given time and the time to recover a given percentage of the initial deformation. A photograph of the EDST used for cable aging assessment on site is shown in FIG. 1.

Certain features of the EDST have been incorporated into the PPT of the present invention. The portable polymer tester of the present invention is compact, has the ability to be used in any orientation and incorporates drive, control, feedback, and force/displacement measurement systems. In accordance with one embodiment of the invention, the PPT further integrates means for using the indentation probe in an oscillation mode to access new parameters such as the specific dynamic stiffness and the amount of lag (or phase) measured between the force and displacement signals.

Figure 2:
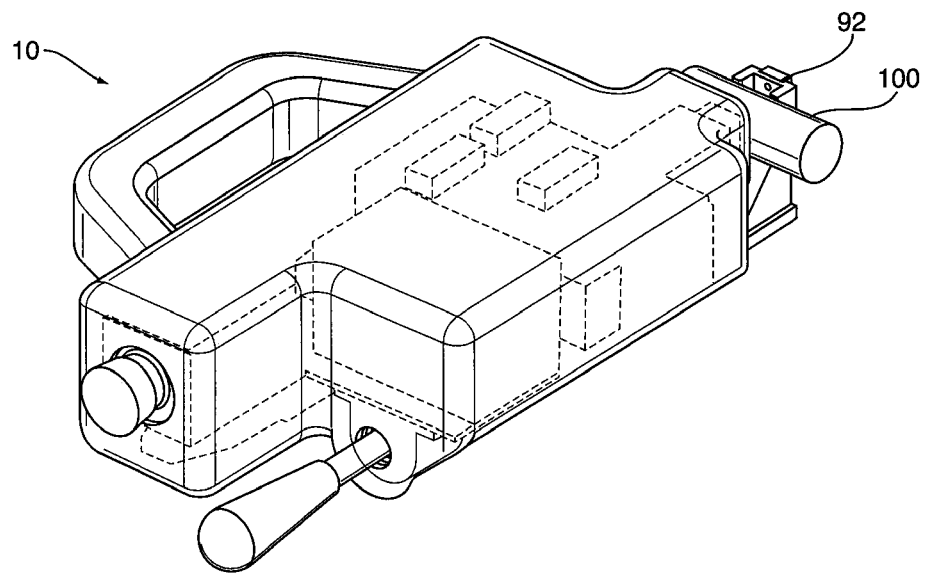
FIG. 2 is a perspective drawing of a portable polymer tester according to one embodiment of the present invention.
Figure 18A:
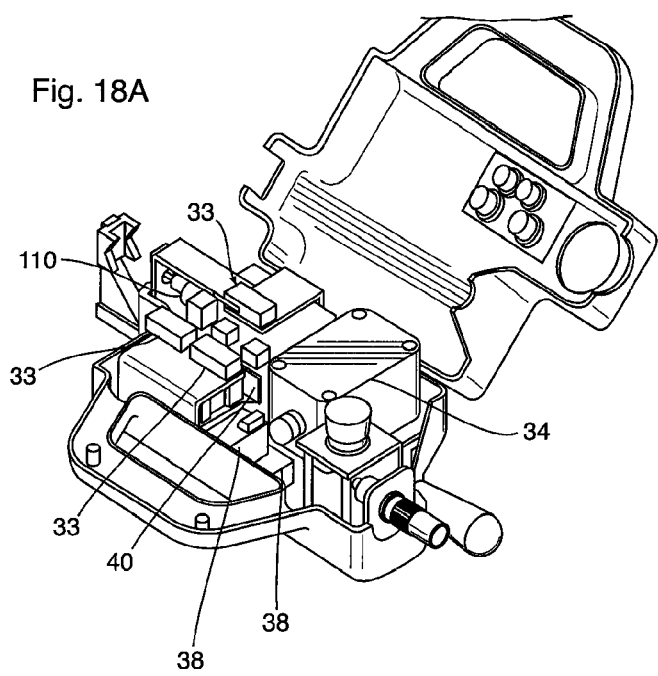
FIG. 18 shows drawings of a portable polymer tester according to one embodiment of the invention, in which the housing is open (18A shows a top perspective view and 18B shows bottom perspective view).
Figure 18B:
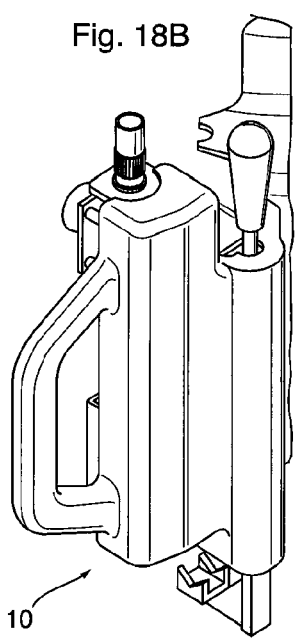

Schematics of PPTs according to specific embodiments of the present invention are provided in FIG. 2 and in FIG. 18. The PPT includes a system for programming the indenter probe displacement profile and controlling the probe position to derive post-indentation parameters. The indentation parameters are similar to those assessed using the EDST. They include the force relaxation (once the material has been indented), and the time to recover a set percentage of initial deformation (once the indenter is quickly retracted to a preset position following the relaxation phase). A typical PPT sequence is outlined in FIGS. 3 and 19, and described in more detail below. The results obtained from the use of PPTs according to the present invention, demonstrate that the PPT has good repeatability and that the test results are consistent with results obtained using the EDST.

Construction of the PPT is made taking into consideration the possible tool exposure to contaminated, above ambient temperature environment when used under extreme conditions, such as at a nuclear site. For example, in accordance with specific embodiments of the invention, the portable polymer tester includes a housing containing the drive, control, feedback, and force/displacement measurement systems, which housing is constructed of material suitable to withstand testing conditions and to protect the interior components from the testing conditions.

Portable Polymer Tester Components:

As noted above, the PPT of the present invention comprises a drive, control, feedback, and force/displacement measurement systems. In addition, the PPT includes a housing surrounding these components, jaw assemblies for holding samples, such as cables, in place during testing, and a probe. The probe can be interchanged with probes of various tip sizes suitable for testing polymer materials with different characteristics. In one example, the probe can be interchanged to accommodate testing of polymer containing-cables with different diameters and polymer jackets. The PPT further includes an internal power source (e.g., a battery) or means for attachment to an external power source (e.g., an AC power plug).

The components of the PPT of the present invention are described in more detail below, with reference to the Figures.

Drive System

The drive system incorporated in the PPT of the present invention includes means for instant or fast retraction of the probe to permit measurement of time of deformation recovery.

The drive system includes a motor, linear slide, high resolution optical encoder system, motion controller and motor driver/amplifier. The arrangement of these components forms a closed-loop control system. More specifically, the motor is preloaded against a manufacturer specified surface that is affixed to the linear slide. This preload force allows the motor to provide a no-slip motion of the slide in any orientation. Moreover, the linear slide includes a scale to allow the measurement of position. The optical linear encoder system comprises a readhead sensor that "reads" the scale and sends the reading to an interpolator in order to increase the positioning accuracy. This position information is then transferred by electrical means to the motion controller. The motion controller employs algorithms to command the motor by way of the motor driver/amplifier until the position error is virtually zero or within an acceptable tolerance, depending on the application of the PPT.

In accordance with one embodiment of the invention, the drive system is manufactured according to the following specifications:

Stage travel of at least 5 mm
Step resolution of about 0.010 μm to about 0.1 μm
Measurement resolution of about 0.010 μm to about 0.1 μm
Motor dynamic stall force of about 30 N to about 34 N
Motor static hold force of about 26 N to about 30 N
Motor operating temperature range of −10 to 50° C.

In accordance with another embodiment, the drive system is manufactured according to the following specifications:

Stage travel of approximately 40 mm
Step resolution to about 10 nm
Measurement resolution: approximately 10 nm
Motor dynamic stall force: about 32 N
Motor static hold force: about 28 N
Motor operating temperature range: about 0 to about 50° C.

In selecting the parts for the drive the overall size and weight of the handheld portion of the PPT needs to be considered as the components will affect both the size and weight of the PPT. Suitable motor types include, but are not limited to voice coil motors, linear shaft motors and ceramic servo motors.

With reference to FIG. 4, a specific example of a drive system 20 of a PPT 10 of the present invention integrates a ceramic servo motor 30 into a nanostage 40, which facilitates instant/fast retraction of the probe 50 during use of PPT 10. Nanostage 40 includes stage table 42 and stage base 44. It is a packaged drive system that eliminates the need for a large number of parts to manufacture or assemble. The stage configuration utilizes a linear slide 60 with crossed roller bearings and a linear optical encoder (not shown). Nanostage 40 is provided completely assembled. Ideally, the ceramic servo motor 70 used is a state of the art device capable of high resolution and high dynamic performance.

Force/Displacement Measurement System

Figure 4A:
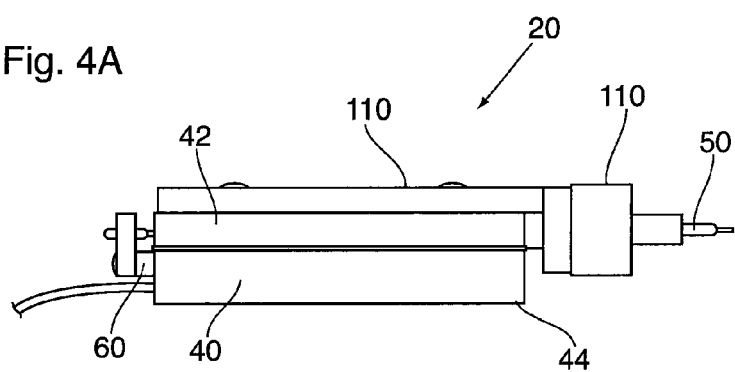
FIG. 4 depicts components of the portable polymer tester of FIG. 2; 4A is a side view of the drive assembly, 4B is a top view of the drive assembly, 4C is a side, cross-section of a part of the tester showing the jaw assembly holding a cable and a probe positioned within a hole in the fixed jaw of the jaw assembly, and 4D is the control chassis for which the portable polymer tester is connected to receive electrical signals, control commands from the motion controller and collect process data that is scaled and transferred to a computer.
Figure 4B:
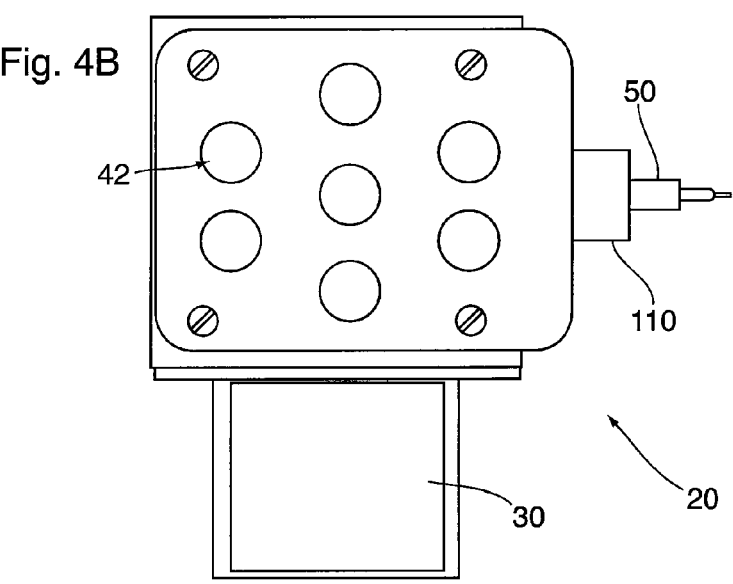

As shown in FIGS. 4A and B, the force/displacement measurement system includes a miniature load cell 110 mounted to the front of the slide and a load cell signal conditioner (not shown) used to measure the force on the probe tip during testing. The linear encoder in the drive system provides the probe position measurement.

Control System

The control system includes a motion controller and a control software program used to provide control and feedback for the force/displacement measurement system. The operating parameters are selected taking into consideration the sample type (e.g., cable type(s)) to be tested (e.g., size, polymer, etc.) and the location(s) or environment(s) of testing. In accordance with a specific embodiment of the present invention, the operating parameters for the PPT are as follows:

Force measurement range of about 0 to about 20 N.
Maximum positioning rate of about 5 mm/s
Minimum positioning resolution of about 0.1 μm.
Oscillation amplitude of about 1 to about 100 μm.
Oscillation frequency of about 0.1 to about 100 Hz.
Operating temperature of about 15 to about 50° C.

A control chassis is used to mount the controller, the motor amplifier, the encoder, the power supplies and a thermocouple transmitter.

Schematics of examples of the motor, linear stage, and chassis of a portable polymer tester are shown in FIGS. 4A-D, 15, 16, 17 and 18.

The test sequence parameters and data collection is controlled using a computer with an appropriate operating system, for example, Windows XP™. In this example, the Windows programming environment is LabVIEW® based by National Instruments Inc.

Indenter Probe

Interchangeable probes having a variety of tip sizes can be used based on the type of polymer or elastomer sample (e.g., cable) tested. The programming options for driving the motion of the tip are very broad and easily adjusted. The input parameters that can be controlled and changed include the preload, the indentation depth, the indentation speed, the type of driving input signal (linear, sinusoidal, etc.), the force relaxation parameters, the deformation recovery parameters. Custom signal profiles can be developed quickly for the purpose of researching new test conditions to enhance the sensitivity to polymer degradation.

Temperature Sensor

The PPT of the present invention optionally includes a temperature sensor.

PPT output parameters that help characterize the tested polymeric material can be significantly affected by temperature, even in the 15 to 30° C. temperature range. Therefore temperature in the tested area of the sample must be accurately monitored. The temperature probe used is, in most cases, a contactless sensor, such as an infrared subminiature thermocouple, that is positioned to measure the surface of the material to be tested just prior to performing an indentation. The temperature information is logged to provide a means of applying correction factors to the indentation data in order to compensate for fluctuations in temperature and when performing subsequent measurements to the same area at a later point in time. It can also provide a means for controlling a heating or cooling apparatus to allow for indentation measurements to be taken at constant reference temperatures. The incorporation of a temperature sensor can improve reliable measurement of the PPT indentation output data.

A temperature sensor mounted on the stage measures the ambient air temperature. Another thermocouple is used to monitor temperature at the motor location. Two miniature thermocouple transmitters mounted on the tool provide an amplified signal to the controller. This eliminates the need for thermocouple extension wires between the tool and the control chassis. An additional temperature sensor and miniature thermocouple transmitter mounted in the control chassis ensures that instrument overheating does not occur.

Sample Retaining Assembly

During testing using the PPT of the present invention, it is often necessary to hold the sample in place. Accordingly, the PPT of the present invention optionally comprises a sample retaining assembly. The configuration and components of the sample retaining assembly will vary based on the application of the PPT and the type of sample to be tested.

Again with reference to FIG. 4, one embodiment of the present invention provides a sample retaining assembly suitable for holding a cable or the like during testing. As shown in FIG. 4C, such a sample retaining assembly can be a jaw assembly 90 that includes a moveable clamping jaw 92 and stationary clamping jaw 94. The jaw assembly further includes means for adjusting the position of the moveable clamping jaw to clamp cable 100 between the two clamping jaws 92 and 94 during testing. As depicted in FIG. 4C, stationary clamping jaw 94 includes through hole 96 through which probe 50 advances to contact and indent the polymer jacket of cable 100.

Indentation Test Using the Portable Polymer Tester

The present invention further provides a method for testing or monitoring polymer aging comprising the steps of:

(a) bringing an indenter probe tip into contact with the polymer, for example a polymer jacket of a cable (the "preload phase");

(b) advancing the indenter probe to deform the polymer while measuring force at the probe tip and displacement of the probe (the "indentation phase");

(c) stopping movement of the probe when a predetermined position is reached;

(d) measuring force exerted on probe tip at the maximum indentation to derive a stiffness or indenter modulus parameter;

(e) holding the probe at a predetermined maximum indentation position to allow polymer force relaxation for a predetermined time of, for example, about 60 s;

(f) retracting the probe quickly (at a speed of approximately 50 to 100 mm/s) to a predetermined intermediate position and monitoring the recovery time until contact with the probe reoccurs (the "recovery phase"); and (g) retracting the probe back to a position out of contact with the polymer jacket and removing the cable.

Figure 19:
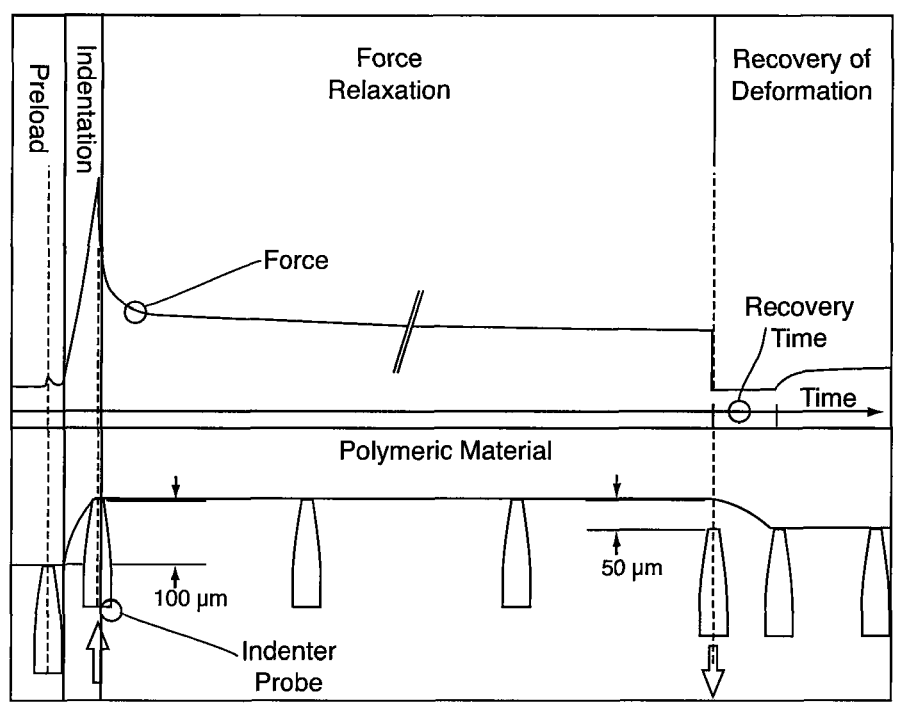
FIG. 19 graphically depicts an indenter test cycle according to one embodiment of the present invention and illustrates the location of the indenter probe during the preload, indentation, force relaxation, and deformation recovery phases of the test cycle.

Steps (a) to (f) are illustrated in the schematic shown in FIG. 19.

For polymer materials that are not too soft, the change in force during indentation is basically proportional to the change in displacement. In this case, the resulting specific compressive stiffness of the polymer is calculated directly using the force and displacement data, where the change in force is divided by the change in displacement.

Figure 5:
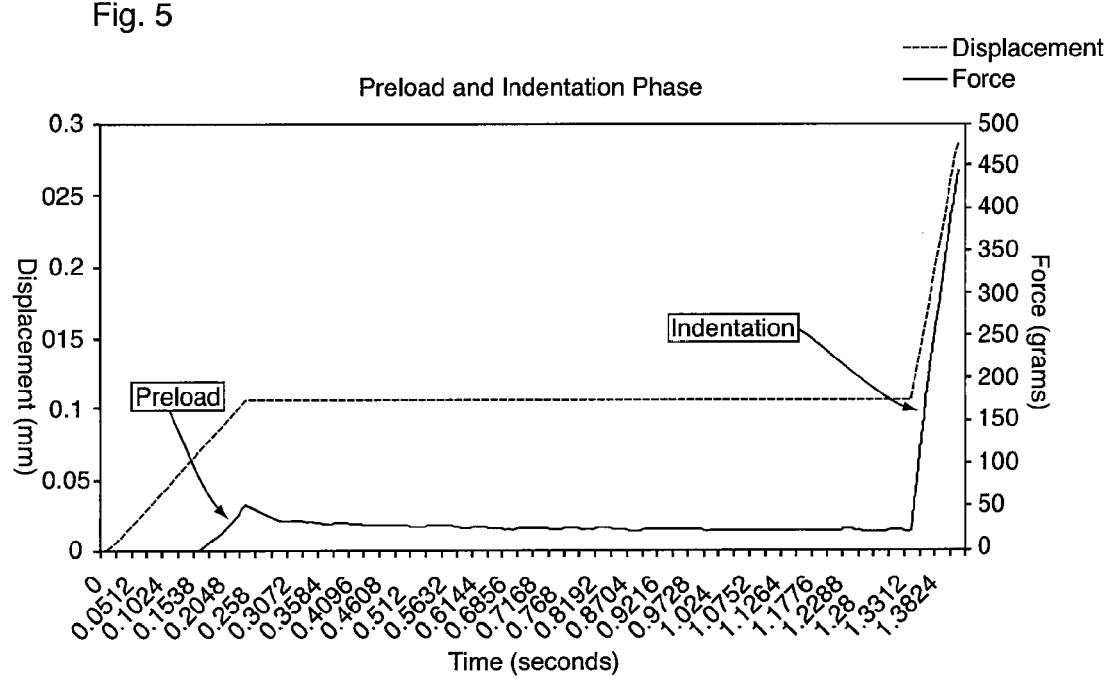
FIG. 5 graphically depicts a preload and initial indentation phase of a test cycle.

As noted above, the indentation phase is preceded by a short small preload phase to bring the indenter tip into contact with the polymer surface. A graphical depiction of force and displacement changes that occur during this stage is provided in FIG. 5.

The PPT of the present invention was developed to perform the method of polymer testing set out above. The PPT offers the option of programming the indenter probe displacement profile and controlling the probe position to derive other post-indentation parameters such as the force relaxation (once the material has been indented), and the time to recover a set percentage of initial deformation (once the indenter is quickly retracted following the relaxation phase). The force relaxation level (and overall shape of the force relaxation curve) does not significantly change when comparing unaged and aged sample characteristics. However, this force relaxation phase will pre-condition the material to show a large difference between unaged and aged samples during the recovery phase.

Figure 6:
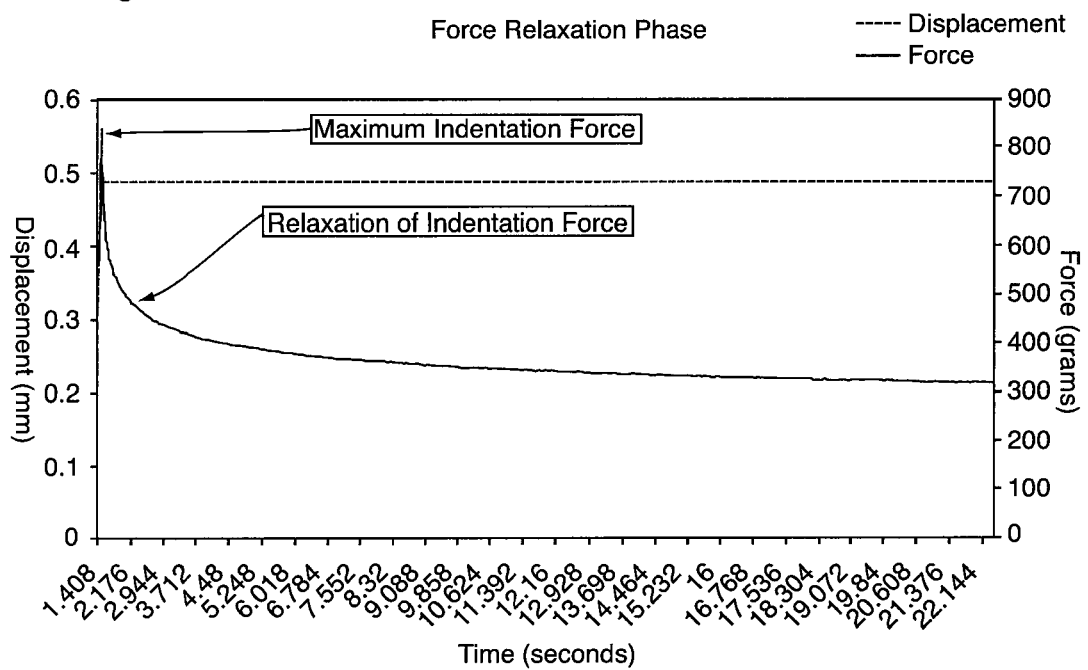
FIG. 6 graphically depicts a force relaxation phase of a test cycle.

A graphical depiction of force and displacement changes that occur during force relaxation phase is provided in FIG. 6.

Figure 7:
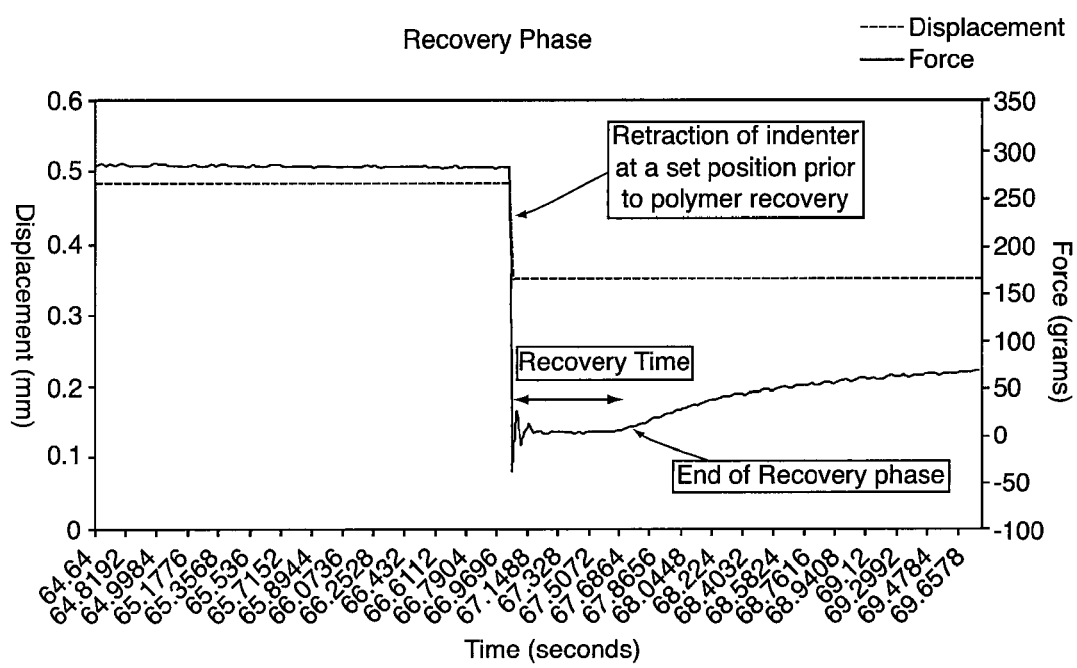
FIG. 7 graphically depicts a recovery phase of a test cycle.

A graphical depiction of force and displacement changes that occur during the recovery phase is provided in FIG. 7. During the recovery phase, the tip is retracted using the controller to a pre-defined position where it waits for the polymer surface to resume contact. This retraction is done quickly such that the probe tip comes briefly out of contact with the polymer to initiate recovery of deformation. The reference percentage of recovery set for the measurement is based on the sensitivity of the technique to material degradation. During this phase, the parameter of interest is the recovery time, or the time that it takes, from initial probe tip retraction, for the material surface to come into contact with the retracted probe tip. Generally, as a result of thermal aging and/or irradiation, the recovery time tends to significantly increase. Therefore, this parameter is very sensitive to polymer degradation resulting from this type of stressors.

The recovery time has now been shown to correlate very well with PVC degradation resulting from increasing irradiation level and increasing thermal aging, especially at percentages of recovery around 35 to 50%. The change in recovery time is similar to the change in tensile characteristics of the material resulting from the effect of irradiation.

Dynamic Oscillation Mode:

The PPT of the present invention can also be used to analyse polymer properties using a dynamic oscillation mode where the input probe displacement is controlled to generate a sinusoidal excitation. For softer materials, the probe remains in contact throughout the entire oscillation period. The simultaneous acquisition of the material reaction force and displacement for the indenter probe over one oscillation period permits further analysis and allows access to other parameters such as the specific dynamic stiffness and a parameter that characterizes the visco-elastic properties of the material (this parameter being derived from the measurement of lag (or phase) that exist between the force and displacement signals in visco-elastic materials).

Figure 8:
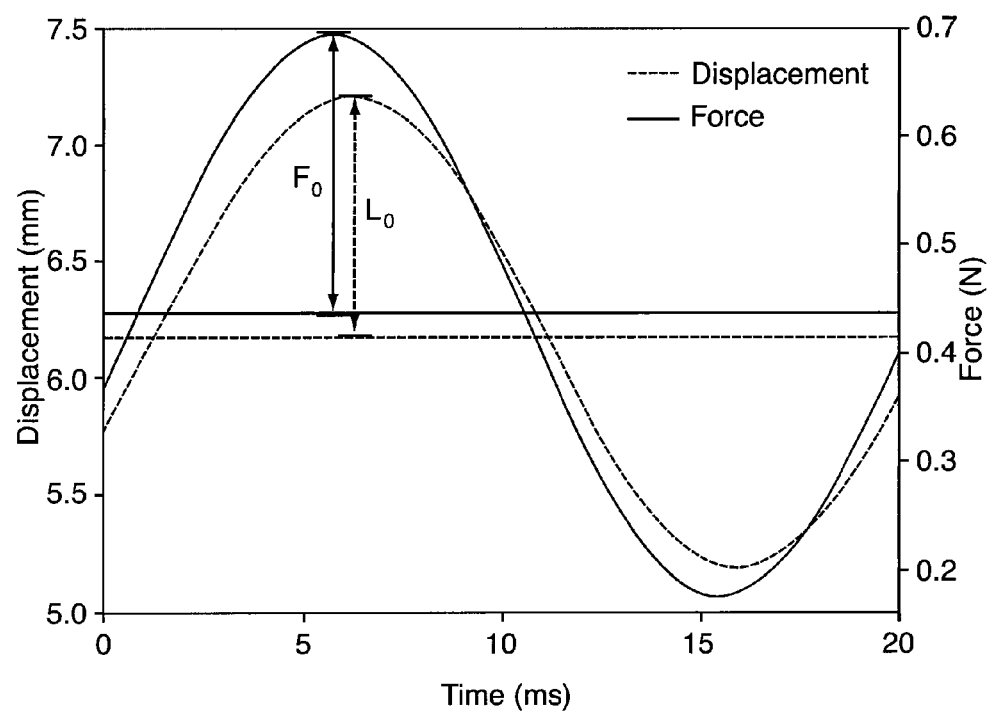
FIG. 8 graphically depicts an indenter probe displacement and reaction force for one oscillation period obtained using a portable polymer tester according to the present invention in the oscillation mode.

When a sinusoidal displacement d is applied to a relatively soft polymeric material using the PPT, the material reaction force F on the indenter probe tip will lag behind the displacement as expressed in the following Equations:

$$d = d_0 \sin \omega t \quad (1)$$

$$F = F_0 \sin(\omega t + \partial) \quad (2)$$

Where t is the time, $F_0$ and $d_0$ are respectively the maximum reaction force and the maximum indentation depth reached during one sinusoidal cycle, $\omega$ is the angular velocity of the sinusoidal oscillations, and $\delta$ is the phase angle (amount that force lags behind displacement). Typical force and displacement time history curves are shown in FIG. 8.

For softer polymeric materials, dynamic stiffness parameters can be derived from the use of the PPT in the oscillatory mode. These parameters can be correlated to the degradation of the material tested. The complex dynamic stiffness k* for a visco-elastic material, as expressed in Equation (3), consists of a real component k' (which is in phase with the imposed sinusoidal displacement d) and an imaginary component k" (which is 90° out of phase with the imposed displacement d).

$$k^* = k' + ik'' \quad (3)$$

The dynamic stiffness parameters can be derived as follows:

$$\text{Absolute dynamic stiffness: } |k^*| = \frac{F_0}{d_0} \quad (4)$$

$$\text{Real component of dynamic stiffness: } k' = |k^*|\cos\partial \quad (5)$$

$$\text{Imaginary component of dynamic stiffness: } k'' = |k^*|\sin\partial \quad (6)$$

For the assessment of material degradation resulting from thermal aging and/or irradiation, a non-dimensional parameter D is defined as follows:

$$D = \frac{k'}{k''} = \frac{1}{\tan\partial} \quad (7)$$

Where D is a parameter characterizing the visco-elastic properties of the tested material. Changes in these properties as a result of thermal aging and/or irradiation usually results in an increase of this visco-elasticity parameter. Therefore, this parameter and the specific dynamic stiffnesses can be used to assess the degradation of softer polymeric materials.

Applications of Polymer Testing

The PPT and method of the present invention are useful in testing and/or monitoring polymer or elastomer properties, often as a measure of age or degradation of the polymer or elastomer. The following is a non-limiting list of polymer or elastomer containing components that can be analysed using the PPT and method of the present invention:

Cable insulations
Cable jackets
O-Rings
Drive Belts
Diaphragms
Gloves
Seals
Gaskets
Hoses
Flat reference slabs of materials for qualification work As described in more detail above, the sample retaining assembly of the PPT can be eliminated or adapted to facilitate analysis of different sample types. For example, the sample retaining assembly will have a different configuration for a tubular sample than a flat sample.

Furthermore, for softer elastomeric materials (seals, o-rings, some gasket materials, etc. . . . ), the oscillatory mode provides a better assessment of material degradation than the classical indenter testing. In oscillatory mode, the dynamic parameters and the degradation factor are used. If the classic indentation test were used in this case it would not be possible to derive a stiffness since there would likely be no linear relationship between force and displacement data measured at various reference times during the indentation. Also the softer elastomeric materials are very bouncy even when aged, therefore the recovery time would be very difficult to measure because it would be very short and recovery time changes would be more difficult to identify between unaged and aged samples.

For harder elastomeric and polymeric materials (cable insulation, cable jacket, hoses, some gaskets materials, some seals materials, etc), the classic indentation test would be used with the stiffness measurement based on simultaneous measurement of force and displacement and within the measurement of recovery time. The oscillatory mode could not be used in this case because the materials would generally not be "bouncy" enough to keep the indenter probe in contact at all times with the material when generating a forced oscillation motion.

The PPT and method of the present invention have broad application, for example, for Material Qualification (manufacturing), Life Extension & Monitoring Programs, Laboratory Materials Research, Preventative Maintenance, etc. As result, the PPT and method can be useful in various fields and industries, such as Energy, Aerospace, Materials Science, Automotive, Military, Chemical Process, all of which make use of polymeric and elastomeric material.

To gain a better understanding of the invention described herein, the following examples are set forth. It should be understood that these examples are for illustrative purposes only. Therefore, they should not limit the scope of this invention in any way.

EXAMPLES

Example 1

Indenter Testing of PVC Cable Jacket Thermally Aged Only

A series of PVC cable jacket samples were thermally aged at 110° C. in a ventilated oven for durations of up to 200 days. The aged samples were then tested using a PPT according to one embodiment of the present invention.

Figure 9:
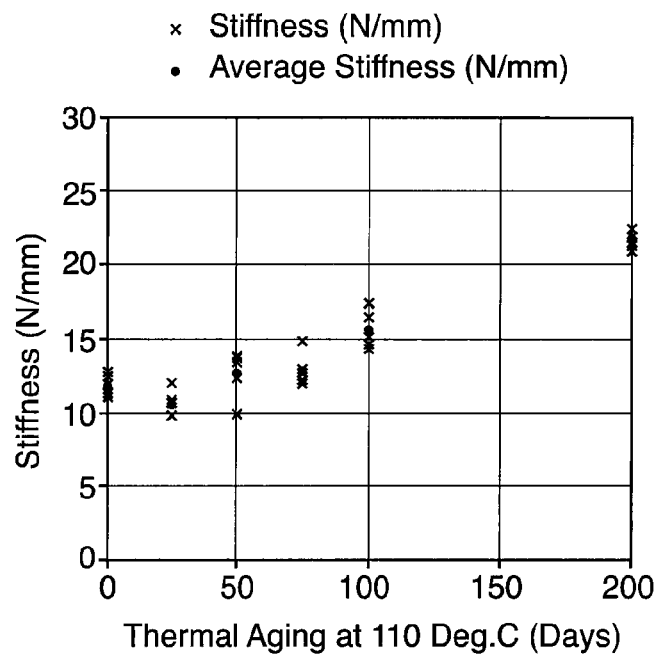
FIG. 9 graphically depicts stiffness results from indenter testing of thermally aged PVC cable jacket.
Figure 10:
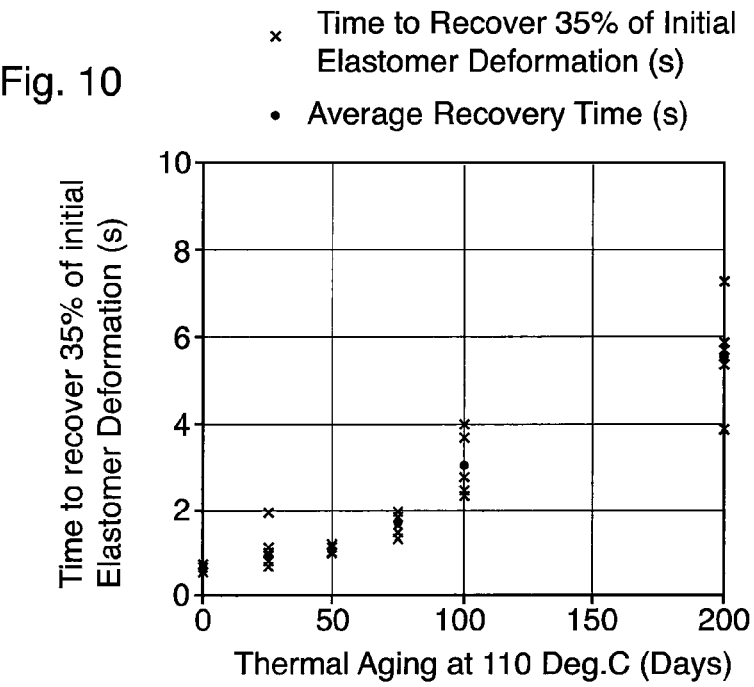
FIG. 10 graphically depicts recovery of deformation data from indenter testing of thermally aged PVC cable jacket.

The specific compressive stiffness results are shown in FIG. 9. There is a gradual change in stiffness as a function of the number of thermal aging days, from 11.9 N/mm for the unaged samples to 21.7 N/mm for samples thermally aged 200 days at 110° C. The time to recover 35% of the initial deformation is shown in FIG. 10. It can be seen that the recovery time is very sensitive to the effect of increased thermal aging duration, with a change of about +75% after 50 days, +167% after 75 days, +392% after 100 days, and +788% after 200 days.

Example 2

Indenter Testing of PVC Cable Jacket Irradiated Only

A series of PVC cable jacket samples were irradiated in a gamma cell at doses ranging from 2 to 60 MRad. The samples were then tested using a PPT according to one embodiment of the present invention and using a standard elongation-at-break method. The dumbbell-shape of PVC cable jacket specimen is placed in the pneumatic grips of a Lloyd LR5K tensile test machine and pulled until failure. The EAB parameter is defined as the percentage increase in elongation at the time of fracture.

Figure 11:
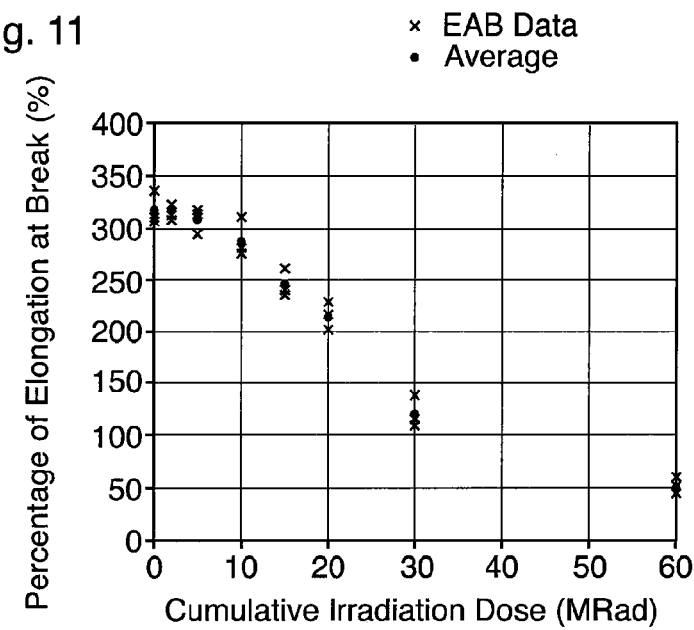
FIG. 11 graphically depicts elongation-at-break data for irradiated PVC cable.

The reference elongation-at-break data for these irradiated PVC cable is shown as a function of irradiation dose in FIG. 11. The graph shows that at 60 MRad the elongation-at-break is down to 50% absolute, a level of degradation that corresponds to the commonly accepted end-of-life point for a cable [IAEA-TECDOC-1188, 2000 (above)].

Figure 12:
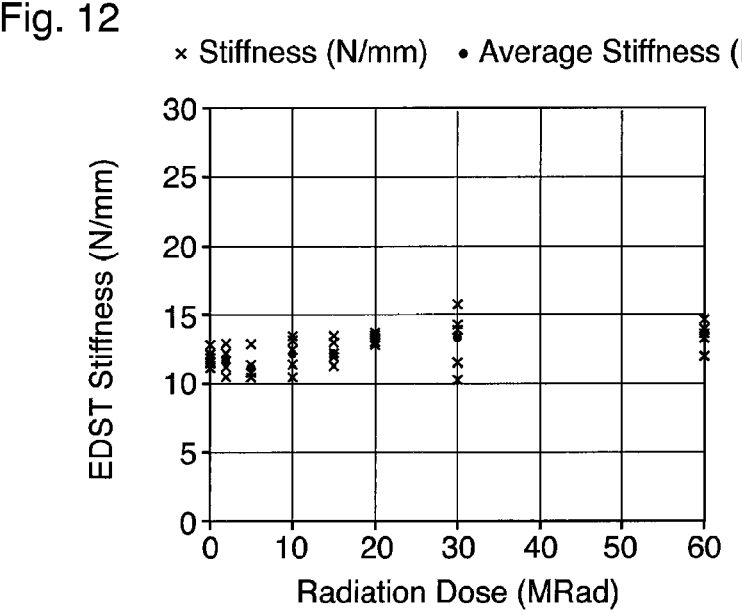
FIG. 12 graphically depicts stiffness results from indenter testing of irradiated PVC cable jacket.

The specific compressive stiffness results for irradiated PVC cable jacket samples are shown in FIG. 12. The stiffness parameter is not sensitive to the degradation resulting from irradiation. This confirms what was found in earlier studies reported in the literature [IAEA-TECDOC-1188, 2000 (above)].

Figure 13:
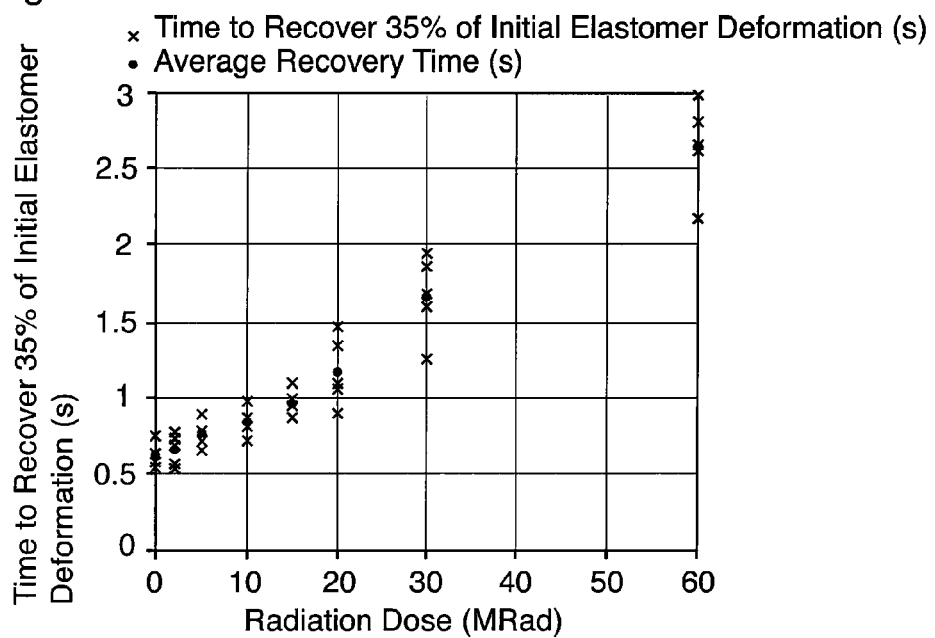
FIG. 13 graphically depicts recovery of deformation data from indenter testing of irradiated PVC cable jacket.
Figure 14:
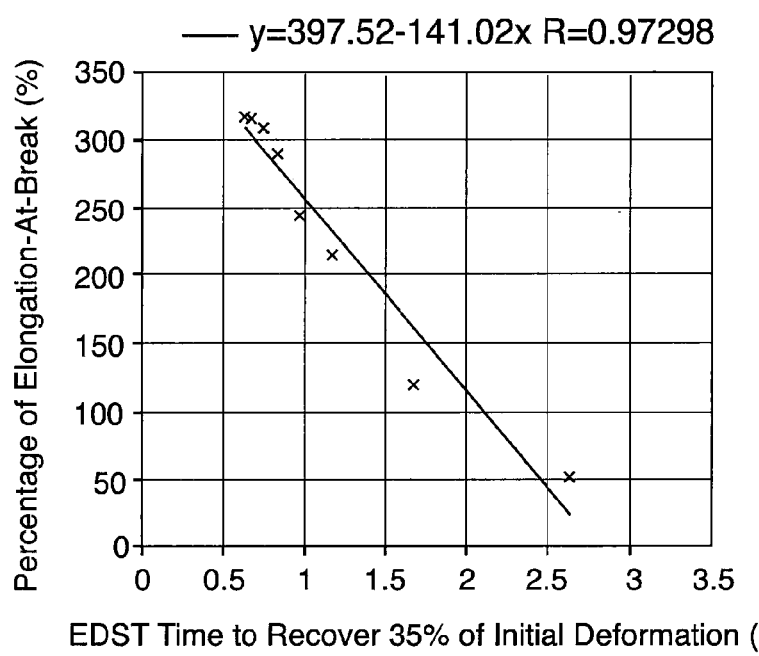
FIG. 14 shows the correlation between the elongation-at-break data from FIG. 13 and the recovery of deformation data from FIG. 13.
Figure 15A:
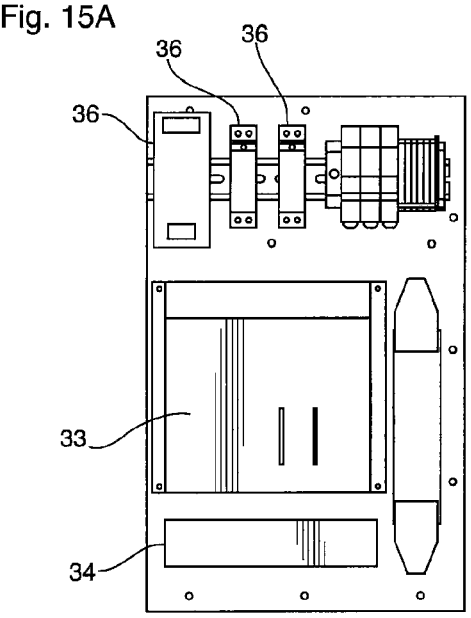
FIG. 15 shows drawings of the back panel of a control chassis showing the mounting and wiring (15A is a face view and 15B is a perspective view).
Figure 15B:
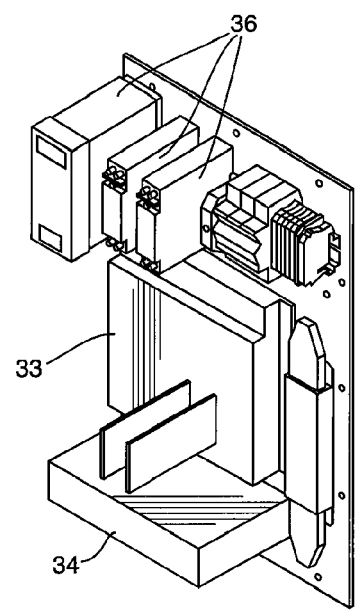
Figure 17A:
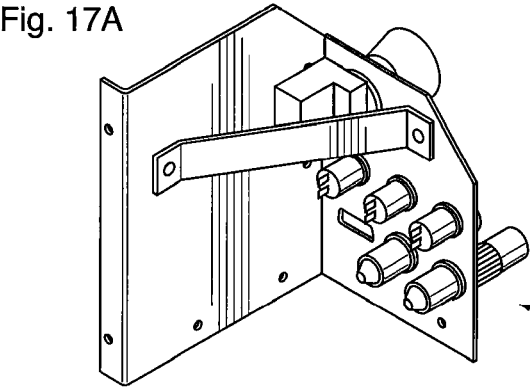
FIG. 17 shows drawings of interior components of a control chassis showing the mounting and wiring (17A is an interior side perspective view and 17B is a top side perspective view).
Figure 17B:
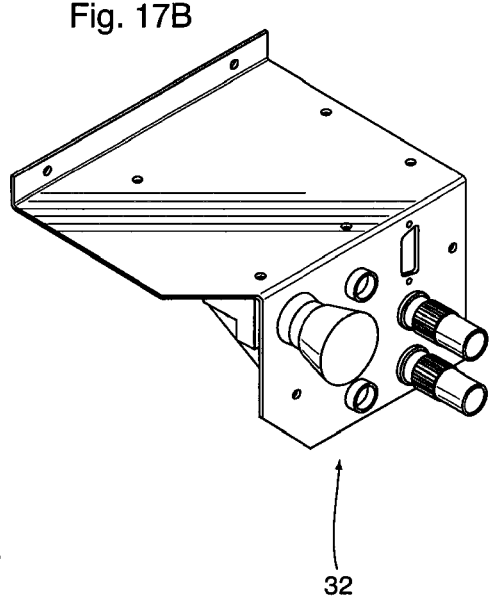

The recovery of deformation data for the same irradiated samples are shown in FIG. 13. The time to recover 35% of the initial deformation increases almost linearly as a function of irradiation dose. From the unaged condition, there is an increase in average recovery time of 33% at 10 MRad, 86% at 20 MRad, 165% at 30 MRad, and 320% at 60 MRad. Therefore, this new approach, utilizing recovery time, provides a means of assessing, for the first time, the degradation of irradiated PVC using an indentation method. Moreover, the deformation recovery time correlates very well with the EAB values measured for the various irradiation levels, with both parameters being extremely sensitive to the material degradation. The good correlation between the elongation-at-break and the time to recover 35% of the initial deformation is shown in FIG. 14.

Example 3

Figure 20:
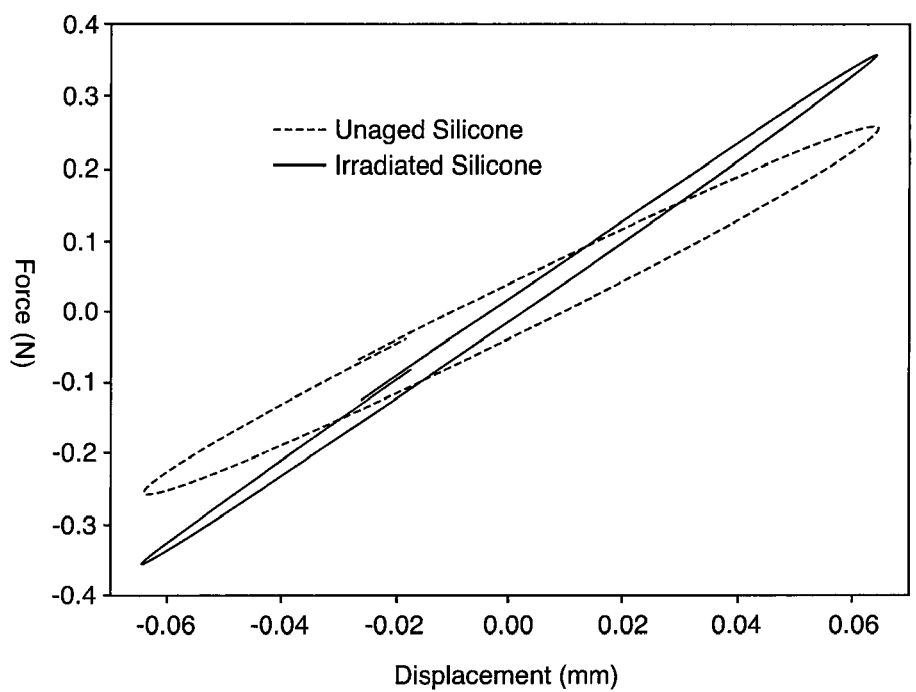
FIG. 20 graphically depicts a phase shift between force and displacement for a silicone door seal material (Lissajous diagram).

Derivation of Dynamic Parameters Using the PPT in Oscillatory Mode for Unaged and Irradiated Silicone Samples The dynamic stiffness parameters and the visco-elasticity parameter D are compared in Table 1 for unaged and 60 Mrad irradiated samples of a silicone door seal material used in nuclear stations. As a result of irradiation, the real component of the dynamic stiffness k' increases from 4.88 to 7.81 N/mm. The imaginary component k" decreases from 0.89 to 0.45 N/mm. The visco-elasticity parameter D increases from 5.48 to 17.3. The force is shown as a function of displacement in FIG. 20 for the unaged and irradiated samples.

TABLE 1

Comparison of dynamic parameters derived using the PPT oscillatory mode for unaged and irradiated silicone samples

| Dynamic Parameters Derived for a 5 Hz Sinusoidal Motion | Unaged Silicone Sample | 70 Mrad Irradiated Silicone Sample |
|---|---|---|
| Real Component of Dynamic Stiffness: k' (N/mm) | 4.88 | 7.81 |
| Imaginary Component of Dynamic Stiffness: k" (N/mm) | 0.89 | 0.45 |
| Absolute Dynamic Stiffness k* (N/mm) | 4.96 | 7.82 |
| Visco-elasticity Parameter $D = \frac{k'}{k''}$ | 5.48 | 17.3 |

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A testing device for measuring physical characteristics of a polymeric or elastomeric material, said device comprising:
   (a) an indenter probe;
   (b) a drive system for effecting movement of said probe, said drive system comprising a motorized linear slide and stage operatively associated with the probe to advance said probe from a first position to a second position to deform said polymeric or elastomeric material, and to effect retraction of said probe to a predetermined intermediate position between said first and second positions;
   (c) a force/displacement measurement system including means for measuring force at the tip of said probe during contact with said polymeric or elastomeric material and means for measuring displacement of the probe; and
   (d) a control system configured to at least temporarily suspend retraction of the indenter probe at the predetermined intermediated position and to continue retraction, in response to sensing engagement between the force displacement measurement system and the polymeric or elastomeric material, after the deformed polymeric or elastomeric material has at least partially recovered.

2. The testing device of claim 1, wherein the control system comprises a motion controller and a motor driver/amplifier.

3. The testing device of claim 1, wherein the motorized linear slide comprises a scale for measurement of position of said linear slide.

4. The testing device of claim 1 additionally comprising a sample retaining assembly for immobilizing all or a portion of the material during testing.

5. The testing device of claim 4, wherein said sample retaining assembly includes a first movable clamping jaw and a second stationary clamping jaw positioned opposite said first jaw.

6. The testing device of claim 1, wherein said drive system comprises a nanostage and a ceramic servo motor.

7. The testing device of claim 1, wherein said means for measuring force comprises a load cell.

8. The testing device of claim 1, wherein said means for measuring displacement comprises an optical linear encoder.

9. The testing device of claim 1 additionally comprising a temperature sensor.

10. The testing device of claim 1, wherein said drive system controls displacement of said probe to generate a sinusoidal excitation.

11. The testing device of claim 1, wherein the drive system provides:
    stage travel of at least 5 mm; and
    a motor operating temperature range of −10 to 50° C.

12. The testing device of claim 1, wherein the predetermined intermediate position is determined as a percentage of the distance between the first position and the second position.

13. The testing device of claim 1, wherein the control system is configured for receiving data and wherein the predetermined intermediate position is based upon the received data.

14. A method of determining visco-elastic properties of a polymer comprising the step of using the testing device according to claim 1 in an oscillatory mode in which said probe displacement is controlled to generate a sinusoidal excitation.

15. The method of claim 14, wherein said visco-elastic properties comprise the absolute dynamic stiffness ($|k^*|$) of said polymer, which is calculated using the following equation:

$$|k^*| = \frac{F_0}{d_0}$$

where:
   $k^*$ is complex dynamic stiffness;
   $F_0$ is the maximum reaction force reached at the probe tip during one sinusoidal cycle; and
   $d_0$ is the maximum indentation depth of the probe reached during one sinusoidal cycle.

16. The method of claim 14 wherein said visco-elastic properties comprise parameter D, which is calculated using the following equations:

$$D = \frac{k'}{k''} = \frac{1}{\tan\delta}$$
$$k' = |k^*|\cos\delta$$
$$k'' = |k^*|\sin\delta$$

where:
   $\delta$ is the phase angle between the sinusoidal displacement of the probe and the sinusoidal reaction force on the probe tip;
   $|k^*|$ is absolute dynamic stiffness;
   $k'$ is a real component of dynamic stiffness; and
   $k''$ is an imaginary component of dynamic stiffness.

17. A method for testing a polymer material aging comprising the steps of:
    (a) deforming a region of the polymer material using a probe;
    (b) calculating specific compressive stiffness of the polymer material from measured displacement of the probe and measured force at the tip of said probe during deformation or at maximum indentation of said polymer material;
    (d) holding said probe to a predetermined indentation depth to allow for force relaxation; and
    (d) retracting said probe to a predetermined intermediate position out of contact with the deformed polymer material and measuring time of recovery of deformation until contact of said polymer material with said probe reoccurs;
wherein the specific compressive stiffness and the time of recovery of deformation are indicators of degree of polymer aging.

18. The method of claim 17 additionally comprising the step of immobilizing the polymer material prior to step (a).

19. The method of claim 17 additionally comprising the step of measuring the temperature of said polymer material.

20. The method of claim 17, wherein said method is repeated over time and correction factors are applied to said indicators of polymer aging to compensate for temperature fluctuations between measurements.

21. The method of claim 17, wherein step (a) comprises a preload phase comprising bringing said probe into contact with said polymer material and an indentation phase comprising advancing said probe to deform said polymer material while measuring force at the tip of said probe during deformation.

22. The method of claim 17, wherein in step (d) the probe is retracted at a speed of from about 50 mm/s to about 100 mm/s.

* * * * *